United States Patent [19]

VandenBerg

[11] Patent Number: Plant 7,446

[45] Date of Patent: Feb. 12, 1991

[54] CHRYSANTHEMUM PLANT NAMED DARK NEOGA

[75] Inventor: Cornelis P. VandenBerg, Salinas, Calif.

[73] Assignee: Yoder Brothers, Inc., Barberton, Ohio

[21] Appl. No.: 409,635

[22] Filed: Sep. 18, 1989

[51] Int. Cl.[5] ..... A01H 5/00

[52] U.S. Cl. ..... Plt./74

[58] Field of Search ..... Plt./74, 75, 76

[56] References Cited

U.S. PATENT DOCUMENTS

| | | | |
|---|---|---|---|
| P.P. 5,924 | 3/1987 | Shoesmith et al. | Plt. 74 |
| P.P. 6,204 | 6/1988 | Hesse | Plt. 74 |
| P.P. 6,312 | 9/1988 | VandenBerg | Plt. 74 |
| 4,616,099 | 10/1986 | Sparkes | 47/58 |

OTHER PUBLICATIONS

Broertjes et al., 1980, "A Mutant of a Mutant of a Mutant of a . . . Irradiation of Progressive Radiation-Induced Mutants in a Mutation-Breeding Programme with *Chrysanthemum morifolium*", Euphytica, 29 (1980): 525-530.

Gosing, ed., 1979, "The Chrysanthemum Manual", The National Chrysanthemum Society, Essex Telegraph Press Ltd., London, pp. 329-336.

Broertjes et al., 1978, "Application of Mutation Breeding Methods in the Improvement of Vegetatively Propagated Crops", Elsevier Sci. Pub. Co., New York, pp. 162-175.

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Dark Neoga particularly characterized by its flat capitulum form; spoon daisy captulum type; red-purple to purple ray floret color; diameter across face of capitulum of up to 14 cm at maturity when grown as a pinched disbudded pot mum; uniform eight week photoperiodic flowering response to short days; medium plant height when grown as a pinched pot mum; recommended both as disbudded and spray pot mum; and spreading and prolific branching pattern.

3 Drawing Sheets

The present invention comprises a new and distinct cultivar of Chrysanthemum, botanically known as *Dendranthema grandiflora*, and referred to by the cultivar name Dark Neoga.

Dark Neoga, identified as 82-350A05, is a product of a mutation induction program which had the objective of creating new Chrysanthemum cultivars that would expand the color range of an existing cultivar while retaining all other traits.

Dark Neoga was discovered and selected by Cornelis P. VandenBerg in December of 1986 in a controlled environment in Salinas, Calif. as one flowering plant within a flowering block established as rooted cuttings from stock plants which had been exposed as unrooted cuttings to an x-ray source of 1,500 rads. The irradiated parent was the cultivar Neoga, disclosed in U.S. Plant Pat. No. 6,312.

The first act of asexual reproduction of Dark Neoga was accomplished when vegetative cuttings were taken from the initial selection in March of 1987 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Dark Neoga are firmly fixed and are retained through successive generations of asexual reproduction.

Dark Neoga has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Dark Neoga, which, in combination, distinguish this Chrysanthemum as a new and distinct cultivar:

1. Flat capitulum form.
2. Spoon daisy capitulum type.
3. Red-purple to purple ray floret color.
4. Diameter across face of capitulum of up to 14 cm at maturity when grown as a pinched disbudded pot mum.
5. Uniform eight week photoperiodic flowering response to short days.
6. Medium plant height, requiring 0 to 7 long days after pinch prior to short days and 1 application of 2500 ppm B-9 SP to attain a flowered plant height of 25 to 35 cm for year-round flowerings when grown as a pinched pot mum.
7. Recommended both as disbudded and spray pot mum.
8. Spreading and prolific branching pattern.

The accompanying photographic drawings show typical inflorescence and leaf characteristics of Dark Neoga, with the colors being as nearly true as possible with illustrations of this type.

Sheet 1 is a color photograph of Dark Neoga grown as a pinched disbudded pot mum.

Sheet 2 is a black and white photograph of three views of the inforescence of Dark Neoga.

Sheet 3 is a black and white photograph showing the upper and under sides of the leaves of Dark Neoga at three stages of development (mature, intermediate and immature).

Of the commercial cultivars known to the inventor, the most similar in comparison to Dark Neoga is the parent cultivar Neoga. All traits of Dark Neoga are similar to those of Neoga, except the color of the ray florets and flower size. The color of the ray florets of Dark Neoga is substantially darker and more intense, and has better color retention under high light and high temperatures than Neoga. The diameter across face of capitulum of Dark Neoga is slightly larger than that of Neoga.

In the following description, color references are made to The Royal Horticultural Society Color Chart. The color values were determined on plant material grown as a pinched disbudded pot mum in Salinas, Calif. on June 7, 1989.

Classification:

*Botanical.*—*Dendranthema grandiflora* cv Dark Neoga.

*Commercial.*—Spoon daisy disbud and spray pot mum.

INFLORESCENCE

A. Capitulum:

*Form.*—Flat.

*Type.*—Spoon daisy.

*Diameter across face.*—Up to 14 cm at maturity.

B. Corolla of ray florets:

*Color (general tonality from a distance of three meters).*—Red-purple (spoons) to purple (tubes).

*Color (upper surface, spoon tips).*—70A to 71A.

*Color (under surface, tubes).*—Between 70C and 75B.

*Shape.*—Base tubular. Distal portion open, flattened and spoon-like.

C. Corolla of disc florets:

*Color (mature).*—2A to 2B.

*Color (immature).*—144B to 144C.

D. Reproductive organs:

*Androecium.*—Present on disc florets only; no pollen.

*Gynoecium.*—Present on both ray and disc florets.

PLANT

A. General appearance:

*Height.*—Medium; 25 to 35 cm as a pinched pot mum with 0 to 7 long days after pinch prior to short days and 1 application of 2500 ppm B-9 SP.

*Branching pattern.*—Spreading and prolific.

B. Foliage:

*Color (upper surface).*—137A to 137B.

*Color (under surface).*—147B.

*Shape.*—Deeply lobed and serrated.

I claim:

1. A new and distinct Chrysanthemum plant named Dark Neoga, as described and illustrated.

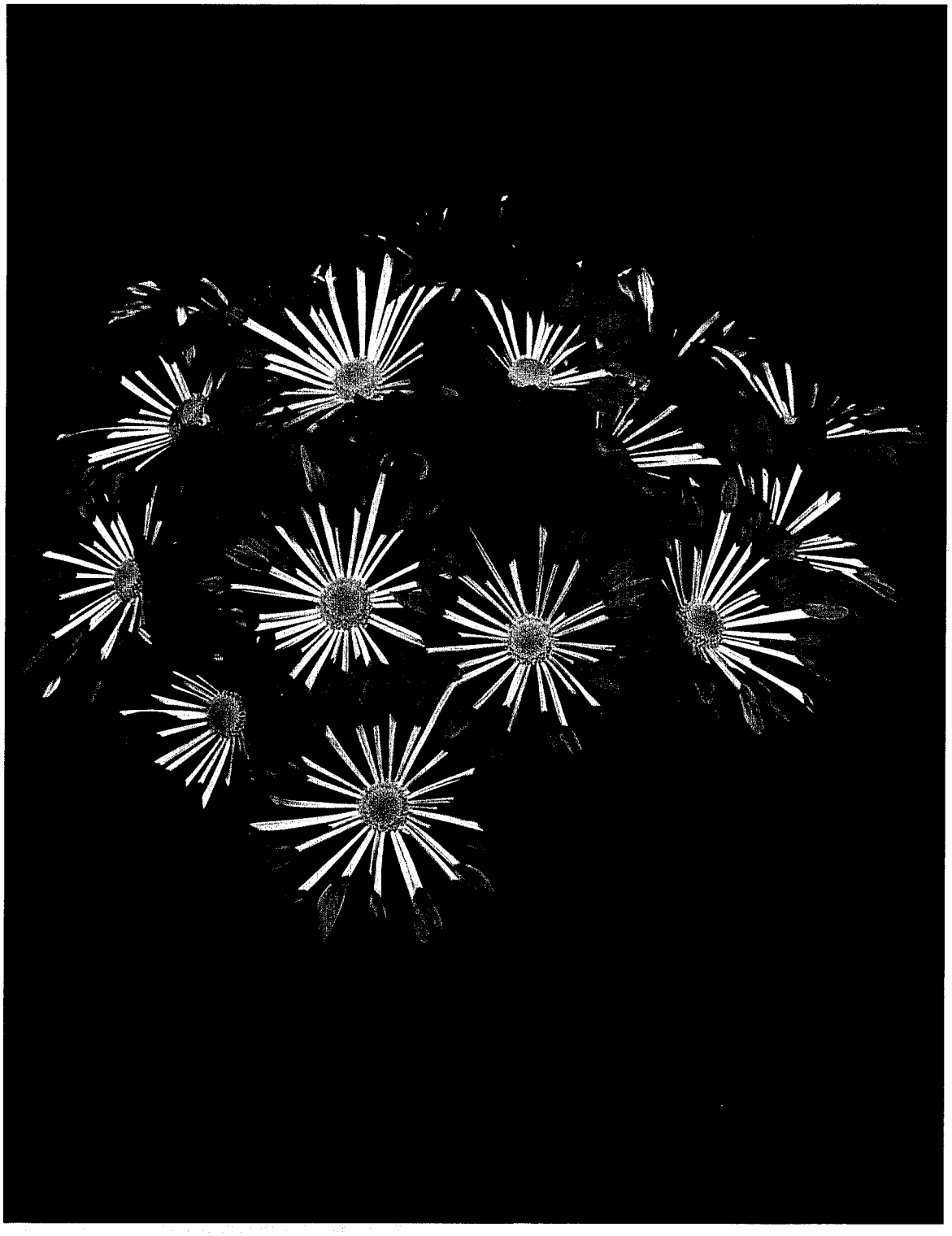

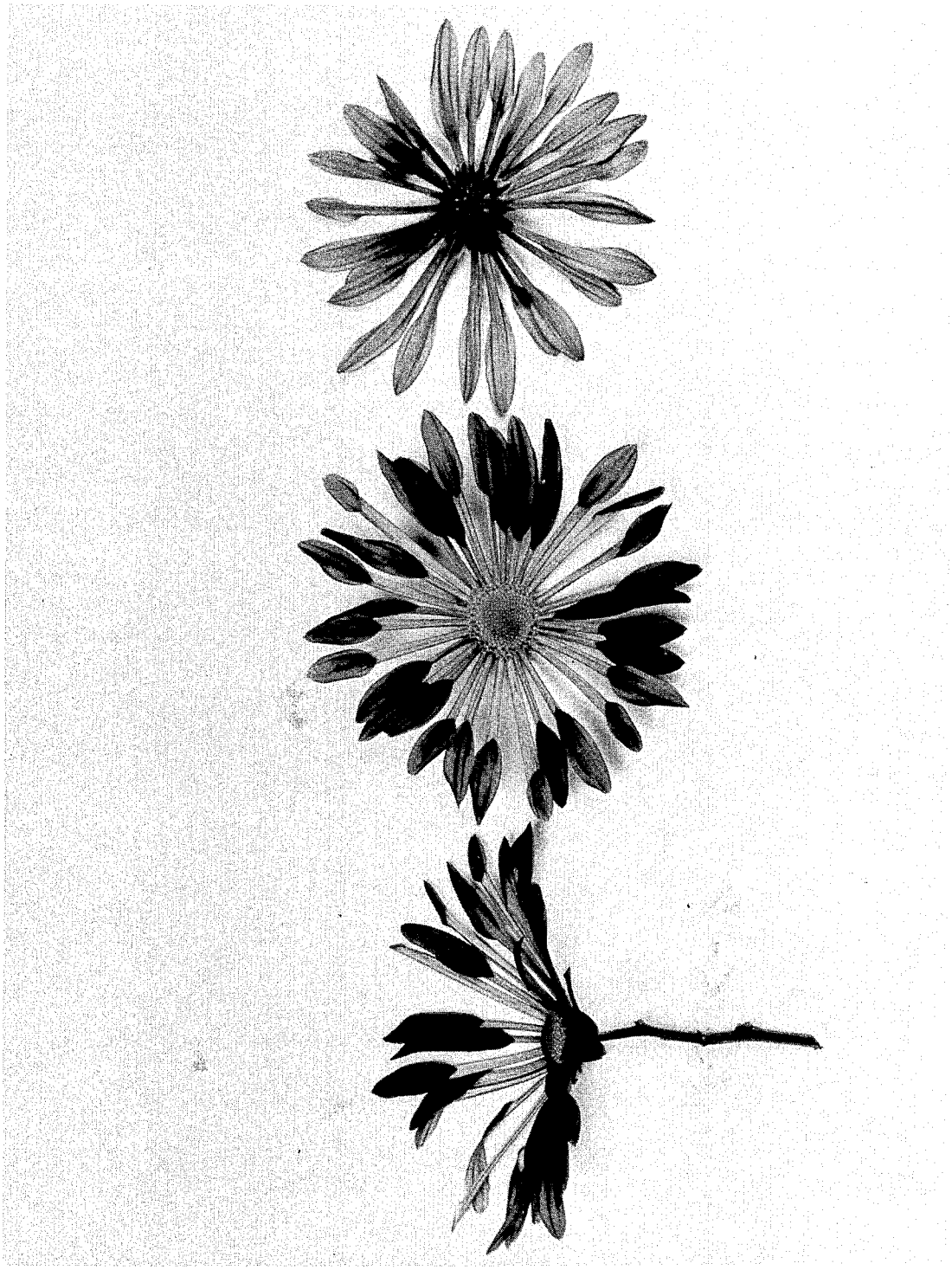

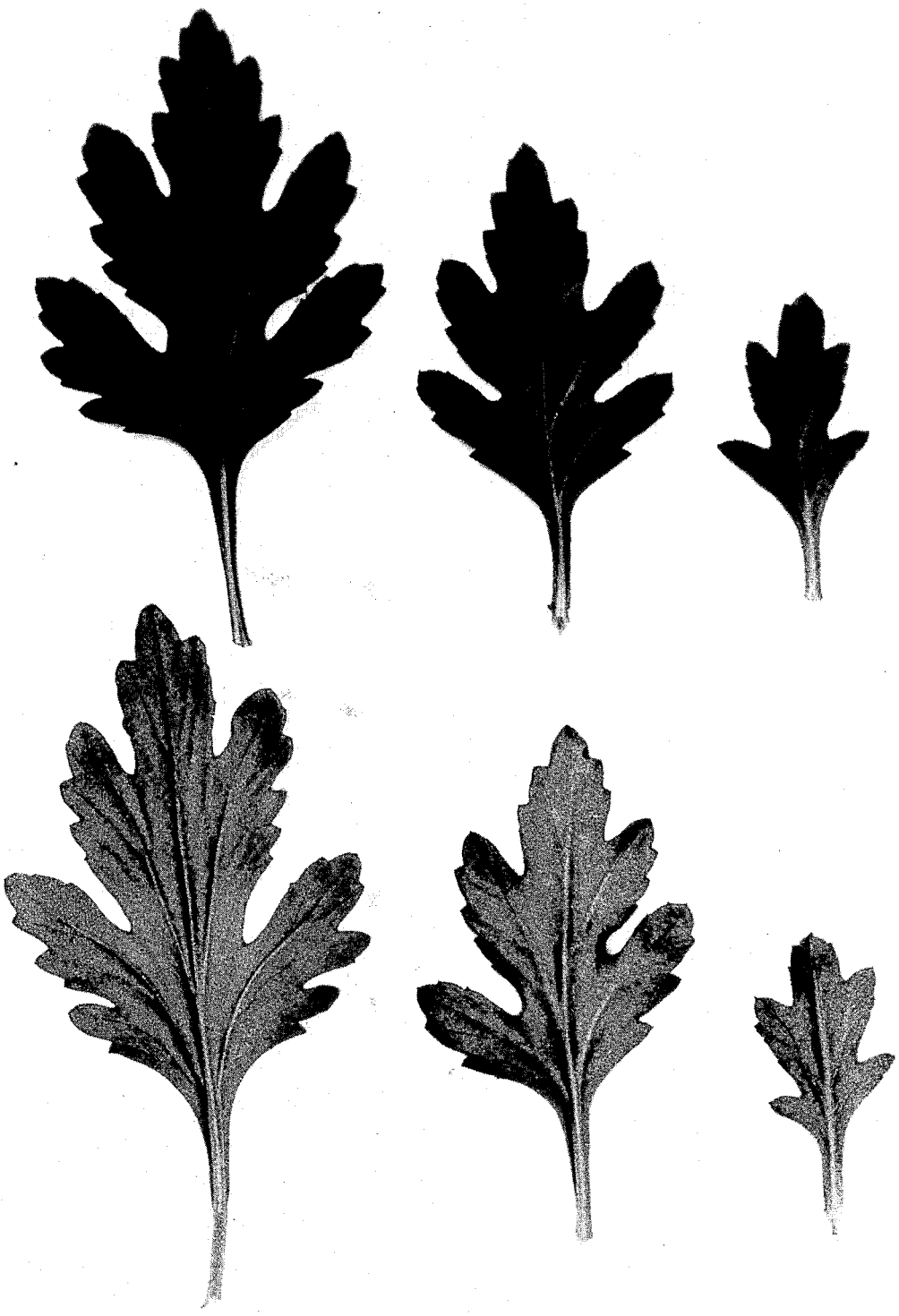

* * * * *